United States Patent [19]
Castellucci

[11] Patent Number: 5,840,935
[45] Date of Patent: Nov. 24, 1998

[54] UNSATURATED POLYMERIZABLE TTF, TCNQ AND DCQDI MONOMERS

[75] Inventor: Nicholas T. Castellucci, San Pedro, Calif.

[73] Assignee: Northrop Grumman Corporation, Los Angeles, Calif.

[21] Appl. No.: 835,689

[22] Filed: Apr. 10, 1997

Related U.S. Application Data

[62] Division of Ser. No. 678,732, Jul. 17, 1996.

[51] Int. Cl.$^6$ ..................................................... C07C 50/06
[52] U.S. Cl. ............................................................ 552/301
[58] Field of Search ............................................. 552/301

[56] References Cited

U.S. PATENT DOCUMENTS

| | | | |
|---|---|---|---|
| 4,036,648 | 7/1977 | Engler et al. | |
| 4,312,992 | 1/1982 | Green. | |
| 4,543,319 | 9/1985 | Chao et al. | 430/312 |
| 4,578,220 | 3/1986 | Huenig | 552/301 |
| 4,769,177 | 9/1988 | Hocker et al. | 252/500 |

OTHER PUBLICATIONS

Nisshin Electric Co. Ltd., Chemical Abstracts, vol. 103, p. 84, #143543k, 1985.

*Primary Examiner*—Christopher Henderson
*Attorney, Agent, or Firm*—Terry J. Anderson; Karl J. Hoch, Jr.

[57] ABSTRACT

Polymeric compositions having inherent electroconductive properties and unsaturated electron-donor and electron-receptor polymerizable monomers for producing such compositions in the form of blends of homopolymers of such monomers or as copolymers of such monomers.

3 Claims, No Drawings

UNSATURATED POLYMERIZABLE TTF, TCNQ AND DCQDI MONOMERS

This is a divisional of copending application(s) Ser. No. 08/678,732 filed on Jul. 11, 1996.

BACKGROUND OF THE INVENTION

1. Field of the Invention

The present invention relates to the preparation of novel flexible thermoplastic polymers which are inherently electroconductive, rather than being doped to impart electroconductive properties thereto, and to novel unsaturated monomers of TTF (tetrathiafulvalene), TCNQ (tetracyanoquinodimethane) and DCQDI (dicyanoquinon diimine) which are polymerizable to form homopolymer blends or copolymers having such properties.

2. Discussion of the Art

The pseudosalt of TTF (tetrathiafulvalene) and TCNQ (tetracyanoquinomethane) is well known as the most (electrically-conductive) organic compound. Its conductivity is metallic-like in that it increases as the temperature of the pseudosalt decreases. The pseudosalt is a charge-transfer complex wherein the donor moiety is the TTF and the electron acceptor moiety is the TCNQ. Reference is made to U.S. Pat. No. 4,036,648.

It is known to impart electroconductive properties to an existing polymer by doping or reacting it with TTF and/or TCNQ, and reference is made to U.S. Pat. Nos. 4,312,992; 4,543,319 and 4,769,177. Polymers produced as disclosed in these patents do not comprise the TTF compound or the TCNQ compound as integral components of the polymer backbone and therefore are less stable, have less temperature-resistant conductivity properties and have lower electroconductivity than the novel polymers of the present invention.

The only known unsaturated derivative of either TTF, TCNQ or DCQDI is vinyl TTF which is disclosed in aforementioned U.S. Pat. No. 4,312,992. However, said patent does not disclose that vinyl TTF is polymerizable, and only discloses coupling the charge-transfer compounds of TTF and TCNQ to existing polymers to produce electroconductive polymers.

SUMMARY OF THE INVENTION

The present invention relates to the discovery of novel polymerizable derivatives of tetrathiafulvalenes (TTF), tetracyanoquinodimethanes (TCNQ) and dicyanoquinodiimines (DCQDI), and to the homo- or co-polymerization of such derivatives to form polymers or polymer blends having excellent inherent electroconductivity properties which are stable and resistant to degradation even at the elevated temperatures encountered during use as electrical materials on advanced aircraft.

The present polymerizable derivatives of TTF donor monomers include, in addition to the known 2- or α-vinyl tetrathiafulvalene, the 2- or α-acetylene TTF and the 2- or α-propenyl TTF, and the corresponding bis derivatives, having an acetylene, vinyl or propenyl substituent at the 2- or α-position of both heterocyclic rings.

The present polymerizable derivatives of DCQDI and TCNQ acceptor monomers include the 2-acetylene, 2-vinyl and 2-propenyl derivatives of 7,8-dicyanoquinodiimine and of 7,7,8,8-tetracyanoquinodimethane, and the 2,5-divinyl and 2,5-dipropenyl derivatives of the 7,8-dicyanoquinodiimines and of the 7,7,8,8-tetracyanoquinodimethanes.

The present polymers include thermoplastic homopolymers and copolymers of said aforementioned polymerizable TTF and TCNQ and DCQDI monomers in which polymerization occurs through the unsaturated radicals. Since the homopolymers of either of said monomers do not contain both the electron donor and the electron acceptor moiety, charge-transfer and pseudo salt-formation cannot occur and the homopolymers are not electroconductive. However, blends of homopolymers of the TTF donor monomer, the TCNQ monomer and/or the DCQDI monomer inter-react ionically to produce charge transfer pseudo salt adducts having strong stable electroconductivity.

Copolymers of the present electron-donor and electron-acceptor monomers, in which copolymerization occurs through the unsaturated radicals of the donor acceptor monomers, are thermoplastic copolymers having inherent strong, stable electroconductivity since the electron-donor and electron-acceptor moieties are connected to the linear or spiral polymer backbone in close proximity to each other to permit charge transfer and pseudo salt formation to occur along the polymer chain.

The following examples illustrate the formation of the monomers of the present invention.

EXAMPLE 1

Preparation of Ethenyl-TCNQ

Tetracyanoquinodimethane is reacted with 1-butyl lithium to introduce lithium into the alpha or 2-position of the ring, followed by reaction with N,N-dimethylformamide to replace the lithium group with an aldehyde group. The TCNQ aldehyde is then converted to 2-ethenyl-TCNQ by a Wittig reaction with methyl triphenyl phosphonium bromide and n-butyl lithium, as illustrated by the following reaction sequence:

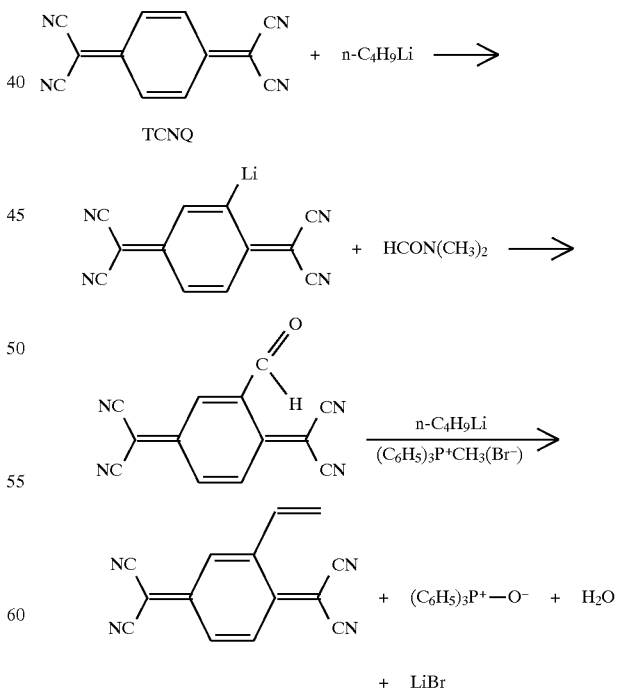

The formed ethenyl- or vinyl-tetracyanoquinodimethane can be homopolymerized by conventional free radical means, using an azo, peroxide, ultraviolet or cationic catalyst in a nitrogen atmosphere to form a solid polymer which does not have electroconductive properties but which can be blended with an electron donor polymer, such as a homopolymer of an α-unsaturated tetrathiafulvalene, to produce a polymer blend charge-transfer adduct having excellent electroconductive properties.

Alternatively, electroconductive copolymers of the 2-unsaturated tetracyanoquinodimethane and the 2- or α-unsaturated tetrathiafulvalene, and/or the 2-or α-unsaturated dicyanoquinondiimine, can be produced by conventional free radical polymerization, using an azo, peroxide, ultraviolet or cationic catalyst and a nitrogen atmosphere. The copolymerization appears to result in the formation of flexible bridging methylene groups which position the donor moieties of the TTF component in close proximity to the acceptor moieties of the TCNQ and/or DCQDI component for favorable π-orbital overlap and electron transfer. The following reaction sequence is illustrative:

EXAMPLE 3

Preparation of 2-(1-propenyl) TTF

Tetrathiafulvalene is lithiated in the 2-position by reaction with n-butyl lithium in tetrahydrofuran solvent at −80° C. (dry ice). The 2-lithium tetrathiafulvalene is then reacted with 3-bromo-1-propene in ether at −80° C. (dry ice) to form 2-(1-propenyl) TTF.

The 2-(1-propenyl) TTF, or 2-allyl TTF, is homopolymerizable by free radical polymerization in the presence of an azo or peroxide catalyst in a nitrogen atmosphere.

The 2-(1-propenyl) TTF homopolymer of Example 3 can be blended in various relative proportions, including 1:1, with the 2-ethenyl (vinyl) TCNQ homopolymer of Example 1 or with the 2-(1-propenyl) TCNQ polymer (allyl) of Example 2, to form polymer blends having excellent electroconductivity properties.

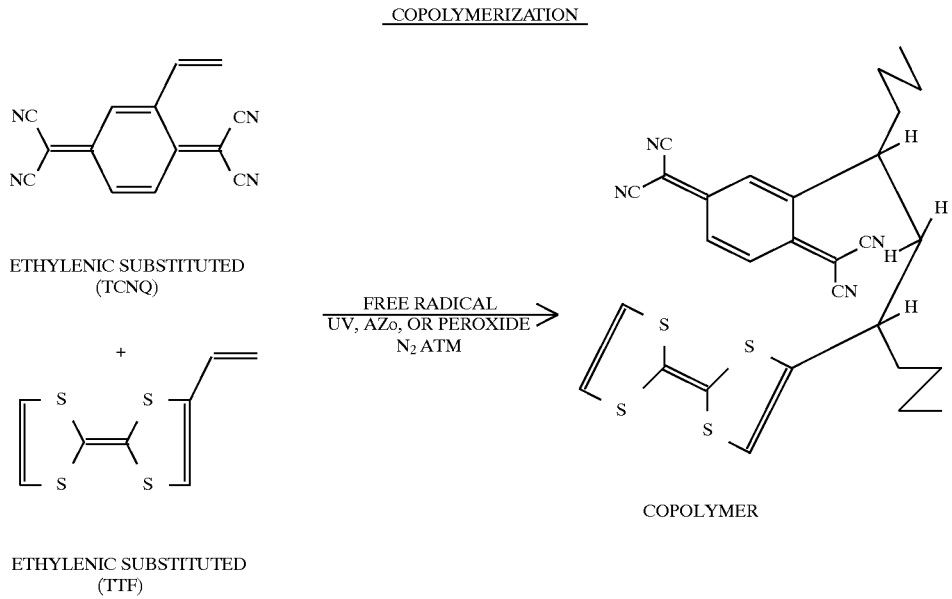

EXAMPLE 2

Preparation of 2-(1-propenyl) TCNQ 2,4-dihydroxy benzoic acid is heated in a water ethanol solvent in the presence of a rhodium on aluminum catalyst in a hydrogen atmosphere to produce 2-carboxy quinone. The 2-carboxy quinone is then reacted with 1-propenyl acetate in the presence of a palladium catalyst, Pd(PPh$_3$)$_4$, to form 2-(1-propenyl) quinone. The 2-propenyl quinone is then reacted with dicyanomethane and aqueous bromine oxide to form 2-(1-propenyl) tetracyanoquinodimethane.

The formed 2-(1-propenyl) TCNQ, or 2-allyl TCNQ, is homopolymerizable and copolymerizable in the same manner as the 2-vinyl TCNQ of Example 1.

Also, the monomer of TTF (Example 3) can be copolymerized with the TCNQ and DCQDI monomers of Example 1 and/or Example 2 to form copolymers having excellent inherent electroconductivity. The following Example 4 illustrates the preparation of 2-allyl (2-propenyl) tetracyanoquinodimethane from 2-allyl-1,4-cyclohexanedione.

EXAMPLE 4

Preparation of 2-Allyltetracyanoquinodimethane

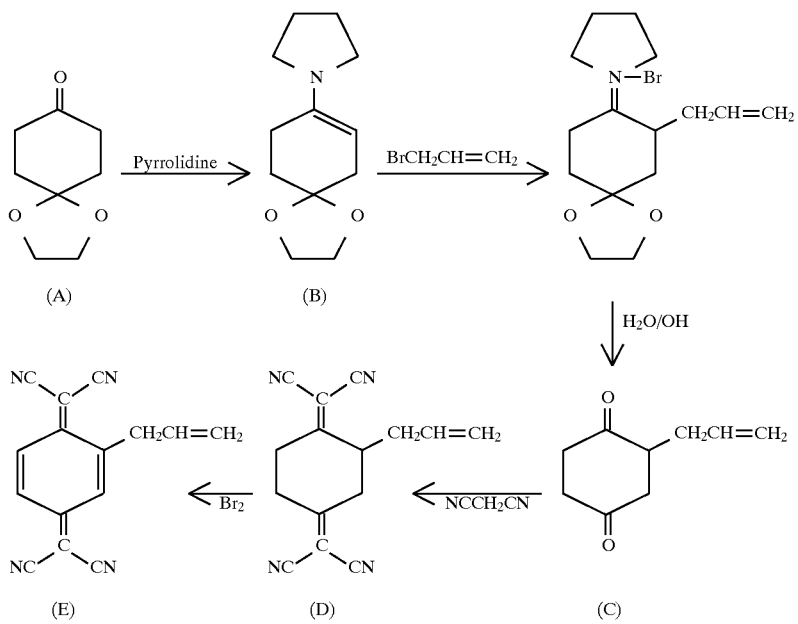

Compound A - 1,4-Dioxaspiro[4.5]decan-8-one

Compound B - 8-Pyrrolidyl-1,4-dioxaspiro[4.5]dec-7-ene

Compound C - 2-Allyl-1,4-cyclohexanedione

Compound D - 2-Allyl-2,3,5,6-tetrahydrotetracyanoquinodimethane

Compound E - 2-Allyltetracyanoquinodimethane

Step I Preparation of the intermediate ammonium salt

A 2-liter, 3-necked flask was equipped with a mechanical stirrer and charged with Compound B, 8-pyrrolidyl-1,4-dioxaspiro [4,5] dec-7-ene (125 g, 0.60 moles). The liquid was then treated with acetonitrile (500 mls, dried over molecular sieves) and allyl bromide (80 g, 0.65 moles). The reaction mixture was stirred and mildly refluxed under nitrogen for three, eight hour periods (not refluxed overnight). Upon cooling, product crystallized. While heating with a water bath, all the solvent was removed under vacuum.

Step II Preparation of 2-allyl-1,4-cyclohexanedione (Compound C)

The solid residue from Step I was mixed with 1000 mls of 10% potassium hydroxide solution and stirred for 48 hours at room temperature. The reaction mixture was then treated with concentrated hydrochloric acid (125 mls) added over a period of 30 minutes. The solution was stirred vigorously for 24 hours at ambient temperature.

The solution was extracted with 4×150 mls portions of diethyl ether. The ether extract was dried over anhydrous magnesium sulfate, then filtered. The filtrate was evaporated to an oil. The residue was transferred to a 200 ml round-bottom flask and any remaining material was washed out using a small amount of ethyl ether. The product was distilled under vacuum as Compound C.

Yield—76 g (75%)
Boiling Point—95–1000° C. (1.0–1.5 mm)
Lot number—1358-P
Carbon-13 nmr—enclosed Reaction III Preparation of 2-Allyl-2,3,5,6-tetrahydro-tetracyanoquinodimethane (Compound D)

A test run was conducted on the preparation of compound D using impure 2-allyl-1,4-cyclohexanedione. Ten grams of allylcyclohexanedione was mixed with 10 g of malononitrile. The mixture was warmed to 90° C., producing a melt. The mixture was kept at 90° C. for ten minutes, then treated with 50 mls of water containing 50 mg of beta-alanine, previously warmed to 90° C. The mixture was stirred vigorously. Slowly, an off-white solid began to form. The reaction mixture was cooled to room temperature and the solid filtered. The product was washed thoroughly with water, then allowed to air dry. The off-white powder was sent for nmr analysis. The nmr is consistent with the formation of Compound D which, under bromination, forms Compound E.

EXAMPLE 5

Preparation of 2-Allyltetrathiafulvalene

Glassware was dried at 120° C. for two hours. Tetrahydrofuran was freshly distilled from sodium/benzophenone. Allyl bromide was dried over 4A molecular sieves and filtered through silica gel before use. A 2-liter, 3-necked flask was thoroughly dried and fitted with a liquid dropping funnel, nitrogen inlet and rubber septum. A magnetic stirring bar was placed in the flask. The flask was then charged with tetrathiafulvalene (13.0 g, 0.064 moles). The system was evacuated and back filled with nitrogen. Tetrahydrofuran (500 mls) was added and the solution stirred until the tetrathiafulvalene dissolved. The solution was cooled to −78° C. using a dry ice/acetone bath. A solution of lithium dimethyamide (3.5 g, 0.064 moles) in 250 mls of tetrahydrofuran was added to the dropping funnel. While stirring, the solution was added dropwise to the reaction mixture over a period of 90 minutes. No visible change was observed. The reaction mixture was allowed to stir for another hour at −78° C., then allyl bromide (9.0 mls) was added, all at once, using a syringe. Again, no visible change was observed.

The reaction mixture was stirred at 78° C. for another hour, then allowed to slowly warm to room temperature. An orange-red solution resulted. The solvent was removed under vacuum.

The residue was dissolved in two liters of ethyl ether and 500 mls of water. The aqueous phase was washed with 2×200 mls of ethyl ether. The organic phases were combined and dried over anhydrous magnesium sulfate. The solvent was then removed under vacuum, leaving a red-brown solid and dark liquid. The residue was added to 500 mls of hexane and shaken. The orange supernatant was decanted. The remaining solid was isolated and analyzed to confirm that it was TTF.

The hexane solution was poured onto a 6" silica gel column. The column was repeatedly washed with hexane until the washing were almost colorless. The column was then washed with methylene chloride, which removed most of the material on the column. The solution was evaporated to dryness leaving an orange oil. Based on the C-13 nmr, the product comprises a mixture of 2,6-diallyl and 2,7-diallyltetrathia-fulvalene.

EXAMPLE 6

Polymerization of Diallyltetrathiafulvalene

DiallylTTF (lot 207-C, ~0.29 g) was dissolved in 20 mls of dry tetrahydrofuran. The solution was treated with ~50 mg of AIBN. The solution was photolyzed with a medium pressure mercury lamp (254 nm) at room temperature and under an atmosphere of nitrogen. Slowly the color changed to orange. After 12 hours the reaction was stopped. The solution was evaporated to dryness leaving a light-brown oily residue. Unlike the starting material, the product was only sparingly soluble in chloroform.

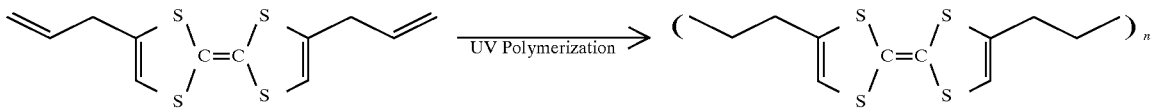

EXAMPLE 7

Polymerization of 2-Allylthetrahydrotetracyanoquinodimethane

2-AllyltetrahydroTCNQ (~1.0 g) was dissolved in 20 mls of tetrahydrofuran forming an orange solution. The solution was treated with ~50 mg of AIBN, then photolyzed with a medium pressure mercury lamp (254 nm) at room temperature and under an atmosphere of nitrogen for 18 hours. No significant change was observed in the color, of the solution. The volatiles were removed under vacuo at 50° C. A waxy, orange solid was isolated.

EXAMPLE 8

Preparation of 2-Propenyl-N,N-dicyano-1,4-quinondiimine

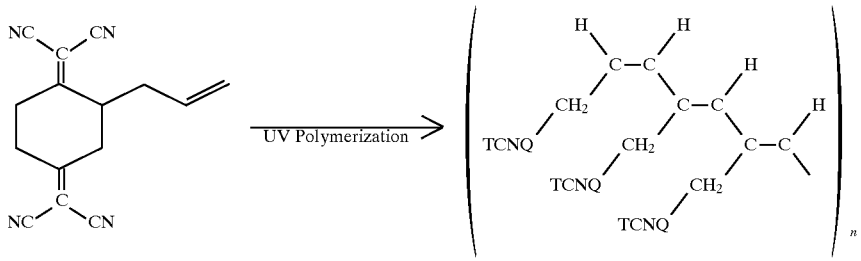

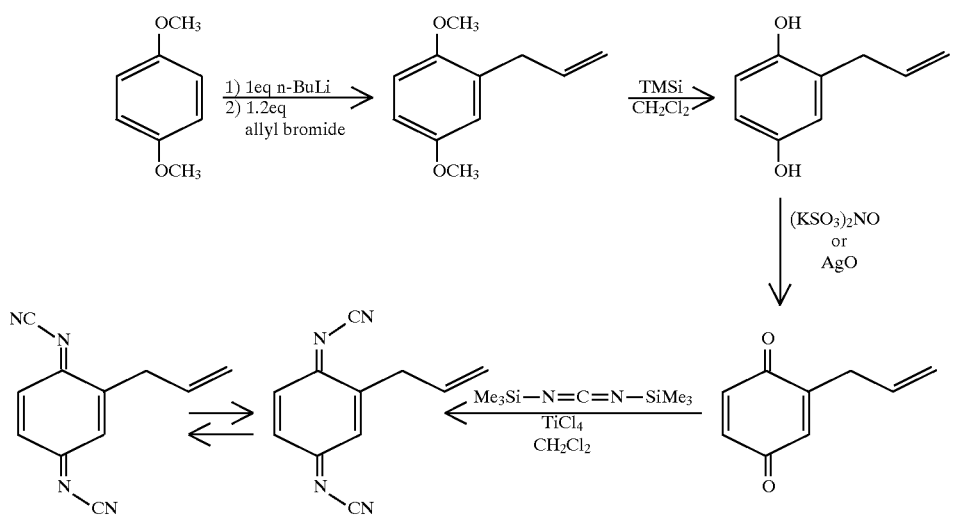

EXAMPLE 9

Preparation of 2-Ethenyl-N,N-dicyano-1,4-quinondiimine

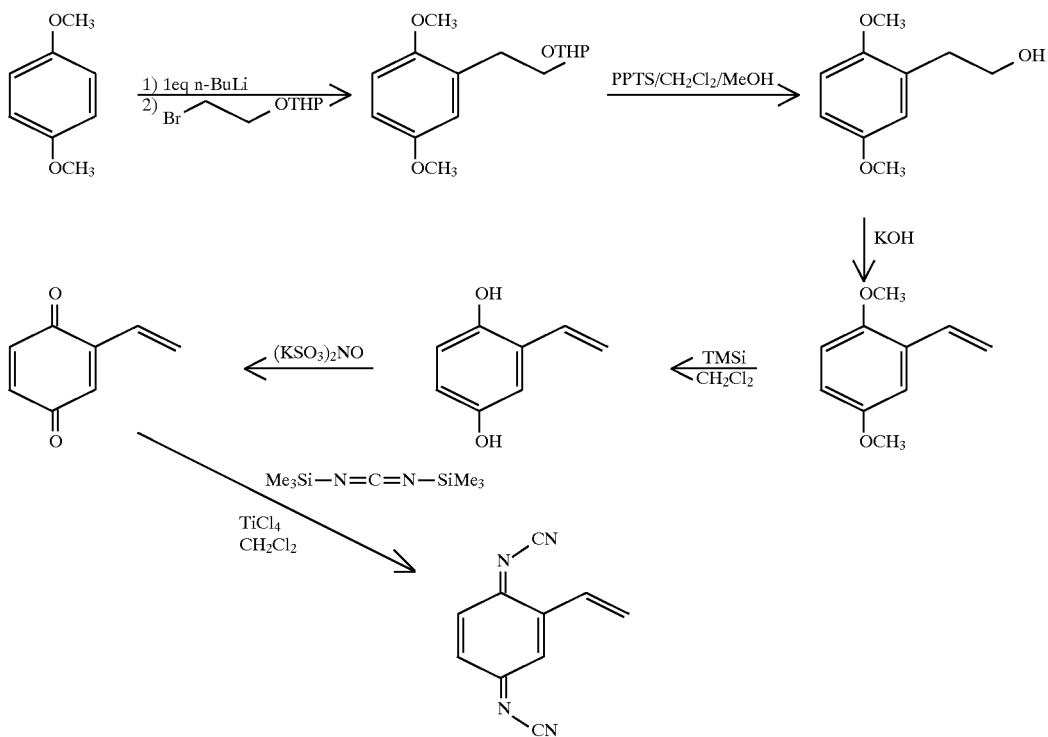

It will also be apparent to those skilled in the art that the present ethylenically-unsaturated monomers can be copolymerized with other ethylenically-unsaturated monomers, such as vinyl monomers, to form a variety of different copolymers having desirable properties imparted by the other monomoers and having electroconductivity imparted by the present TTF, TCNQ and DCQDI monomers.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A polymerizable monomer having the formula:
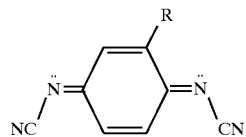
in which R is selected from the group consisting of $CH_2=CH-$, and $CH_2=CH-CH_2-$.
2. A monomer according to claim 1, comprising 2-ethenyl-N,N-dicyano-1,4-quinondiimine.
3. A monomer according to claim 1, comprising 2-propenyl-N,N-dicyano-1,4-quinondiimine.
* * * * *